US009946847B2

(12) United States Patent
Pallai et al.

(10) Patent No.: US 9,946,847 B2
(45) Date of Patent: Apr. 17, 2018

(54) LIBRARIES OF COMPOUNDS HAVING DESIRED PROPERTIES AND METHODS FOR MAKING AND USING THEM

(71) Applicant: BIOBLOCKS, INC., San Diego, CA (US)

(72) Inventors: Peter V. Pallai, San Diego, CA (US); Warren S. Wade, San Diego, CA (US)

(73) Assignee: BIOBLOCKS INC., San Diego, CA (US)

( * ) Notice: Subject to any disclaimer, the term of this patent is extended or adjusted under 35 U.S.C. 154(b) by 130 days.

(21) Appl. No.: 14/430,042

(22) PCT Filed: Sep. 20, 2013

(86) PCT No.: PCT/US2013/060970
§ 371 (c)(1),
(2) Date: Mar. 20, 2015

(87) PCT Pub. No.: WO2014/047463
PCT Pub. Date: Mar. 27, 2014

(65) Prior Publication Data

US 2015/0269356 A1 Sep. 24, 2015

Related U.S. Application Data

(60) Provisional application No. 61/704,479, filed on Sep. 22, 2012, provisional application No. 61/786,343, filed on Mar. 15, 2013.

(51) Int. Cl.
*G01N 33/48* (2006.01)
*G06F 19/00* (2018.01)
(Continued)

(52) U.S. Cl.
CPC ......... *G06F 19/706* (2013.01); *C07D 401/04* (2013.01); *C07D 403/04* (2013.01);
(Continued)

(58) Field of Classification Search
None
See application file for complete search history.

(56) References Cited

U.S. PATENT DOCUMENTS

| | | |
|---|---|---|
| 7,416,524 B1 | 8/2008 | Lobanov et al. |
| 2002/0049548 A1 | 4/2002 | Bunin |

(Continued)

FOREIGN PATENT DOCUMENTS

| | | |
|---|---|---|
| WO | 1998024760 A1 | 6/1998 |

OTHER PUBLICATIONS

Search Report from International Application PCT/US2013/060970, dated Apr. 2, 2015.

*Primary Examiner* — Larry D Riggs, II
(74) *Attorney, Agent, or Firm* — Greer, Burns & Crain; Gregory P. Einhorn; Arik B. Ranson

(57) ABSTRACT

In alternative embodiments the invention provides libraries of compounds, or drugs or drug candidates, manufactured and selected for having a desired property such as a biological or a chemical activity, and methods for making and using them. In one embodiment, the invention provides methods for identifying desirable compounds from very large compound sets using a compound fragment as the query. In alternative embodiments, the invention provides methods of making compounds, and libraries of compounds, using a "feasible reaction" growth scheme.

16 Claims, 3 Drawing Sheets

(51) Int. Cl.

| | |
|---|---|
| ***C07D 405/04*** | (2006.01) |
| ***C07D 401/04*** | (2006.01) |
| ***C07D 403/04*** | (2006.01) |
| ***C07D 409/04*** | (2006.01) |
| ***C07D 417/06*** | (2006.01) |
| ***C07D 498/04*** | (2006.01) |
| ***C07D 498/20*** | (2006.01) |
| ***C40B 30/02*** | (2006.01) |
| ***G06F 3/048*** | (2013.01) |

(52) U.S. Cl.

CPC ......... *C07D 405/04* (2013.01); *C07D 409/04* (2013.01); *C07D 417/06* (2013.01); *C07D 498/04* (2013.01); *C07D 498/20* (2013.01); *C40B 30/02* (2013.01); *G06F 3/048* (2013.01)

(56) References Cited

U.S. PATENT DOCUMENTS

2004/0083060 A1 4/2004 Church et al.
2004/0265909 A1 * 12/2004 Blaney ............... G01N 33/6803 435/7.1

* cited by examiner

LIBRARIES OF COMPOUNDS HAVING DESIRED PROPERTIES AND METHODS FOR MAKING AND USING THEM

RELATED APPLICATIONS

This application is a national phase application claiming benefit of priority under 35 U.S.C. § 371 to Patent Convention Treaty (PCT) International Application serial number PCT/US2013/060970, filed Sep. 20, 2013, which claims benefit of priority to U.S. Provisional patent application Ser. Nos. 61/704,479, filed Sep. 22, 2012, and Ser. No. 61/786,343, filed Mar. 15, 2013, which are expressly incorporated by reference herein in their entirety for all purposes.

FIELD OF THE TECHNOLOGY

The invention generally relates to synthetic and medicinal chemistry, and drug discovery. In alternative embodiments the invention provides libraries of compounds, or drugs or drug candidates, manufactured and selected for having a desired property such as a biological or a chemical activity, and methods for making and using them. In one embodiment, the invention provides methods for identifying desirable compounds from very large compound sets using a compound fragment as the query. In alternative embodiments, the invention provides methods of making compounds, and libraries of compounds, using a "feasible reaction" growth scheme.

BACKGROUND

Currently, methods such as virtual screening have been used to identify a set of compounds with potential biological activity to serve as the starting points for drug discovery. Starting with a large set of chemical structures in electronic format, these methods identified a small subset with a higher probability of interaction with the system of interest by applying a series of filters to the initial set, including but not limited to 2-D similarity to a query molecule, 3-D similarity to a query molecule, chemical property limits such as Lipinski's rule of 5, and docking to an experimental or a theoretical bio-molecular target structure. Because it is practically impossible to enumerate and filter all possible real-world structures, there is a continuing need to limit the size of the initial structure set and provide new methods for identifying a manageable subset of the overall chemistry space so that virtual screening and target assay screening can be performed.

We have previously described the concept of the SYNTHEVERSE™ (Bioblocks, Inc. San Diego, Calif.) chemistry space (see, e.g., Virtually screening the Syntheverse: Finding new leads from synthetically feasible libraries; Lemmen, et al., Abstracts of Papers, 241st ACS National Meeting & Exposition, Anaheim, Calif., United States, Mar. 27-31, 2011 (2011), COMP-11), which is the collection of all compounds that can be made by current synthetic methods. Every compound contained in the SYNTHEVERSE™ is the product of at least one synthetic scheme and is connected to at least one set of starting materials that could be used to make it. By nature, this subset is still impractically large and continuously growing as new synthetic methods are discovered.

A given implementation of the SYNTHEVERSE™ can be biased towards the desired endpoint for the structures, for example, an implementation designed to contain compounds with potential biological activity can be designed to avoid functionality known to cause problems in biological systems. Alternatively, implementation of the SYNTHEVERSE™ can be biased toward a particular class or classes of final product structures, for example, compounds that can be constructed from commercially available starting materials. Alternatively, implementation of the SYNTHEVERSE™ can be biased towards a specific use of the product compounds, for example, an implementation designed to contain compounds with potential high temperature superconductivity will contain potential products containing multiple metal ions. However, a biased SYNTHEVERSE™ is still too large to enumerate; even a two-step reaction sequence with limited starting materials can generate millions of potential products, and the number of products grows exponentially with the number of starting materials and reaction steps.

Known methods include screening a SYNTHEVERSE™ chemistry space using FEATURETREES™ (BioSolveIT GmbH, Sankt Augustin, Germany) similarity to identify compounds similar to a query, using a known compound with high activity against at least one biological target, and using an available crystal structure. The structures are encoded as fragments and built stepwise into a set of final structures, choosing those that are similar to the query. A practically-sized set of product molecules, for example 10,000, similar to the original query in size and complexity, are then filtered through a virtual screening protocol to identify compounds with potential to interact with the target of the original query.

Fragment Based Lead Discovery is a set of recent methods that provide alternative starting points (e.g., for lead compound s) for drug discovery. Compared to the products of either virtual or target assay screening, the identified compounds are both less complex and more efficient at binding their target. As such, they serve as higher quality starting points for the identification of drug candidates with the properties required for safe and effective use in humans. Application of cycles of synthetic expansion, modification and biological assay feedback generate compounds with the potency to be used as a lead compound for a traditional drug discovery effort.

SUMMARY

In alternative embodiments the invention provides methods or processes for making or identifying a plurality or a library of compounds having a desired property, such as a biological activity or chemical property, or a method for making or identifying a drug or a lead compound having a desired property, such as a biological activity or chemical property, comprising:

(1) (a) providing a chemistry space, or a plurality of synthesizable product molecules, or a plurality of synthetic compounds, wherein the synthesizable product molecules are defined or described as a set of reactions, or a set of "feasible" reactions, with a set of reagent sets or starting materials associated with each reaction, and each reaction step of each reaction sequence is encoded separately so that intermediate structures are available as products in the chemistry space, and optionally, the step (a) also, or further, comprises:

(i) encoded separately for each reaction, a set of starting materials that produce products (compounds) that cannot be used in subsequent steps of the reaction scheme, (ii) selecting reagent sets or starting materials associated with a particular reaction in a chemistry space, or a SYNTHEVERSE™ chemistry space, so that all or substantially all possible combinations define feasible reactions;

(iii) wherein the starting materials comprise carboxylic acids, carboxylic acid chlorides, primary amines, secondary amines, sulfonyl chlorides, alcohols, aldehydes, ketones, alkyl halides, aryl halides, boronic acids, trialkyl tin reagents, nitriles, isonitriles, imidates and the like as determined by the requirements of the reaction itself; or, (iv) wherein the reactions comprise: palladium mediated cross-coupling reactions such as the Suzuki, Negishi and Stille reactions, amine acylation, amine sulfonylation, nucleophilic displacement of an aromatic halogen, reduction, oxidation, alkylation of an amine, oxygen or carbon nucleophile, reductive amination, the Mitsonobu reaction, the Cadogan reaction, olefin metathesis, heterocyclic ring condensations, electrophilic aromatic substitution and the like; or step (a) further comprises: steps (i) and (ii); steps (i) and (iii); steps (i) and (iv); steps (ii) and (iii); steps (ii) and (iv); steps (iii) and (iv); steps (i), (ii) and (iii); steps (ii), (iii) and (iv); steps (i), (iii) and (iv); and steps (i), (ii), (iii) and (iv);

(b) providing a fragment or a substructure of a fragment, and searching the starting material set of the chemistry space or a plurality of synthesizable product molecules of step (a) by (using) the fragment or substructure, and identifying a subset of starting materials that contain the fragment or fragment substructure, and optionally, the step (b) also, or further, comprises:

(i) wherein the fragment or substructure of the fragment comprises a single ring or ring assembly or equivalent, (ii) providing a set of simpler fragments (fragments of less complex structure) generated from an original (starting) structure, e.g., by stepwise removal of some or all atoms not contained in a ring or an equivalent structure, (iii) the fragment (for example, in alternative embodiments, is a single ring or a ring assembly), is used to search the starting material by substructure, and a subset of starting materials is identified that contain the fragment or the fragment substructure, (iv) a fragment comprises or consists of a single ring system that binds with only mM affinity to its target, and optionally the fragment has an ligand efficiency >0.5 kcal/mol/heavy atom, (v) the set of all possible combinations that contain at least one non-ring atom can be used to search the starting material set of the space by substructure to generate the starting material subset, or any combination or all of (i) to (v);

(c) generating product (compound) structures from the identified starting materials in step (b) in all reactions where they are used directly (in a one-step reaction scheme), wherein optionally, because this is a one-step reaction scheme, the number of products per reaction is limited by the number of starting materials; and (d) filtering the products (compounds) from step (c) to a manageable number (filtering the products from step (c) to a lesser number, or selecting a subset of the products (compounds) from step (c)) for a virtual screen or a synthesis and an assay or a combination thereof, wherein optionally possible filters comprise: a reactive functional group removal, property limits, clustering and selection, random percent selection, or a combination thereof, thereby making or identifying a plurality or a library of compounds, or a drug, having a desired property or a desired biological activity or chemical property; or (2) a process or method as set forth in FIG. 1, FIG. 3, or a process or method as set forth in FIG. 1 and FIG. 3.

In alternative embodiments, the filtered products are further screened by a virtual screen or actual screening assay for purchased or synthesized compounds to identify products with (having) a desirable profile or a desirable property such as a biological activity or chemical property.

In alternative embodiments, any product (compound) identified in step (d) (above) or after the filtered products are further screened is used in a query of step (b) (above), wherein the reactions being searched contain the product (compound) as a starting material and new products (compounds) identified can be synthesized by a reaction scheme of two steps or more. In alternative embodiments, the process is applied again to any product thus generated, and identifying a small subset of interest related to the initial fragment out of the entire chemistry space.

In alternative embodiments, the process is repeated for all fragments and/or compounds of interest, or having a desired property or biological activity or chemical property, to provide or generate a set of compounds with the desirable profile (e.g., the desired biological property or activity or chemical property) derived from the original chemistry space, wherein optionally these products retain the design characteristics of the original chemistry space and are associated with a reaction scheme for their synthesis and the required starting materials.

The invention provides methods for making or identifying a plurality or a library of compounds having a desired property, such as a biological activity or chemical property, or a method for making or identifying a drug or a lead compound having a desired property, such as a biological activity or chemical property, comprising:

(1) (a) providing a fragment or a substructure of a fragment (for example, in alternative embodiments, a single ring or ring assembly) for which a substructure search of the starting material set of the space described herein (e.g., as described above), above returns no hits;

(b) determining the reactions where this fragment or substructure could react and is used directly;

(c) generating the product structures using the structure described in step (a) as the only representative of its reagent list and all the starting materials used for the other lists in each reaction identified in step (b), and optionally, where this is a one-step reaction scheme and the fragment is not present in the original space, the number of products per reaction is limited by the number of starting materials of the other reactant types; and (d) the products from step (c) are filtered to a manageable number for a virtual screen or synthesis and assay, and optionally filters comprise reactive functional group removal, property limits, clustering and selection, or random percent selection, or a combination thereof;

(2) the method of (1), further comprising: wherein the filtered products are then further screened by a virtual or actual screening assay to identify products with desirable profiles;

(3) the method of (1) or (2), wherein any product identified can then be used as a query for step (1)(a), and optionally, the reactions being searched contain the product as a starting material and the new products identified can be synthesized by a reaction scheme of two steps or more, and optionally, where the original starting material was not in the chemistry space, the generated products were also not present in the original chemistry space;

(4) the method of any of (1) to (3), wherein the process can be applied again to any product of step (3), identifying a small subset of interest related to the initial fragment that are an extension of the original chemistry space;

(5) the method of any of (1) to (4), further comprising: the process can be repeated for any fragment that contains functionality that can react in the reaction schemes described for the space, leading to a set of compounds with desirable profiles (e.g., a biological or a chemical property or activity) (these products extend the design characteristics of the original space but are still associated with a reaction scheme for their synthesis and the required starting materials);

(6) the method of any of (1) to (5), further comprising: product structures are generated from the identified starting materials in all reactions where they are used in a primary intermediate (an intermediate made only from described starting materials)

and optionally, where this is a two-step reaction scheme, the number of intermediates per reaction is limited by the number of starting materials in the other reagent lists, and optionally, the smallest number of products that contains each of the possible starting materials is generated, optionally, if the two-step reaction scheme is:

A+B→Intermediate C

C+D→product E and there are 5 A starting materials, 10 B starting materials and 24 D starting materials, then the total number of products E is 5×10×24=1200, optionally, if $A_3$ is the starting material of interest, then there are 240 possible E containing all the combinations of B and D, optionally if intermediate C is enumerated 24 times to give $A_3B_1$, $A_3B_2$ . . . $A_3B_{10}$, $A_3B_1$, . . . $A_3B_{10}$, $A_3B_1$, . . . $A_3B_4$, C is then combined with each individual D to generate 24 E: $A_3B_1D_1$, $A_3B_2D_2$, . . . $A_3B_{10}D_{10}$, $A_3B_1D_{11}$, . . . $A_3B_{10}D_{20}$, $A_3B_1D_{21}$, . . . $A_3B_4D_{24}$.

In alternative embodiments, the invention provides method for making or identifying a plurality or a library of compounds having a desired property, such as a biological activity or chemical property, or a method for making or identifying a drug or a lead compound having a desired property, such as a biological activity or a chemical property, comprising:

(a) providing a fragment or a substructure of a fragment for which a set of related compounds is desired by comparison to a calculated property or properties, and optionally, the fragment or a substructure comprises a single ring or ring assembly;

(b) determining the desired range of each property relative to the value calculated for the initial query, optionally each calculated property consists of a molecular weight, a ring count, a AlogP or another property that can be calculated on a per fragment or per atom basis, optionally the desired range of each property comprises a lower or higher molecular weight, a lower or higher ring count, a lower or higher AlogP, or equivalents, and optionally the desired range of each calculated property may not contain the value calculated for the initial query;

(c) generating all product structures that match the calculated property ranges;

wherein optionally:

(i) for each library, the properties are corrected for the changes produce by each reaction so that the properties measured are based on the product to be generated (because this query has no structural component, the number of products depends on the size range of the desired properties), (ii) the number of products that will be generated can be determined before enumeration and the ranges adjusted until a manageable number can be produced;

(iii) the product structures from step (c) are filtered to a manageable number for a virtual screen or synthesis and assay, and optionally the filters comprise: a reactive functional group removal, property limits, clustering and selection, or random percent selection, or a combination thereof; and (iv) further screening the filtered product structures by a virtual screen or actual screening assay for purchased or synthesized compounds to identify products with desirable profiles;

(v) the product structure identified in step (iii) or step (iv) is used as a query for step (b), and optionally, the properties ranges used are for the product of the previous steps, and optionally the process can be applied again to any product so identified, (vi) identifying a small subset of interest with properties related to the initial fragment out of the entire chemistry space;

(vii) repeating step (b) and any one of, or subset of, or all of steps (i) to (vi), for all fragments of interest, leading to a set of compounds with desirable profiles (optionally a biological property or a chemical activity) derived from the original chemistry space, wherein the products retain the design characteristics of the original space and are associated with a reaction scheme for their synthesis and the required starting materials.

The invention provides computer-implemented methods comprising a method of the invention, or a subset of any methods of the invention.

The invention provides computer program products for implementing a method of the invention, or a subset of any methods of the invention.

The invention provides computer program products for processing data, the computer program product comprising: a computer-executable logic contained on a computer-readable medium configured for causing the following computer-executed step to occur: the computer-implemented method of the invention, or, a computer program product of the invention. The computer-executable logic can be further configured to cause the following steps to occur: receiving data elements or structures; and storing the data elements or structures in a memory, and optionally transmitting the identified structures, or plurality or library of compounds having the desired property.

The invention provides Graphical User Interface (GUI) computer program products comprising a representation of the compounds and/or fragments used or identified in a method of the invention, or the plurality or library of compounds having a desired property as made or identified in a method of the invention, or a plurality or library of compounds of the invention.

The invention provides computer systems comprising a processor and a data storage device, wherein said data storage device has stored thereon: (a) a computer program product for implementing a computer-implemented method of the invention; (b) a computer program product of the invention; (c) a Graphical User Interface (GUI) computer program product of the invention; or, (d) a combination thereof.

The invention provides a non-transitory memory medium comprising program instructions for running, processing and/or implementing: (a) a computer program product for implementing a computer-implemented method of the invention; (b) a computer program product of the invention; (c) a Graphical User Interface (GUI) computer program product of the invention; or, (d) a combination thereof.

The invention provides a computer-readable storage medium comprising a set of or a plurality of computer-readable instructions that, when executed by a processor of a computing device, cause the computing device to run, process and/or implement: (a) a computer program product for implementing a computer-implemented method of the invention; (b) a computer program product of the invention; (c) a Graphical User Interface (GUI) computer program product of the invention; or, (d) a combination thereof. In alternative embodiment, the invention provides computer-readable storage medium comprising or having stored thereon a plurality or library of compounds of the invention.

The invention provides computer program storage devices, embodied on a tangible computer readable medium, comprising: (a) a computer program product for implementing a computer-implemented method of the invention; (b) a computer program product of the invention; (c) a Graphical User Interface (GUI) computer program product of the invention; or, (d) a combination thereof. In alternative embodiment, the invention provides computer program storage devices comprising or having stored thereon a plurality or library of compounds of the invention.

The invention provides computers or equivalent electronic systems, comprising: a memory; and a processor operatively coupled to the memory, the processor adapted to execute program code stored in the memory to: run, process and/or implement: (a) a computer program product for implementing a computer-implemented method of the invention; (b) a computer program product of the invention; (c) a Graphical User Interface (GUI) computer program product of the invention; or, (d) a combination thereof. In alternative embodiment, the invention provides computers or equivalent electronic systems comprising or having stored thereon a plurality or library of compounds of the invention.

The invention provides systems, comprising: a memory configured to: store structures or values associated with a plurality of structures or data points and/or a plurality of structures or data elements, and a processor adapted to execute program code stored in the memory to: run, process and/or implement: (a) a computer program product for implementing a computer-implemented method of the invention; (b) a computer program product of the invention; (c) a Graphical User Interface (GUI) computer program product of the invention; or, (d) a combination thereof. In alternative embodiment, the invention provides systems comprising a memory comprising or having stored thereon a plurality or library of compounds of the invention.

The invention provides a compound, or a plurality of compounds, or libraries of compounds, made by a method of the invention, e.g., a computer-implemented method of the invention, wherein optionally the compounds comprise compounds having a biological or a chemical activity, or are lead compounds, or are drug candidates. In one embodiment, the library is a virtual library and the virtual compounds are stored in a database. In one embodiment, a library of starting materials and/or reactions used to practice this invention are stored on a database. A database of the invention can be stored on a system, computers or equivalent electronic systems, computer program storage devices, computer-readable storage medium and the like. In alternative embodiments, the invention provides systems, computers or equivalent electronic systems, computer program storage devices, computer-readable storage medium and the like comprising or having stored therein or thereon a database of the invention, and/or a compound, or a plurality of compounds, or libraries of compounds, made by a method of the invention.

All publications, databases, patents, and patent applications cited in this specification are herein expressly incorporated by reference as if each was specifically and individually indicated to be incorporated by reference.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The following drawings are illustrative of aspects of the invention and are not meant to limit the scope of the invention as encompassed by the claims.

Like reference symbols in the various drawings indicate like elements.

DETAILED DESCRIPTION

Figure 1:
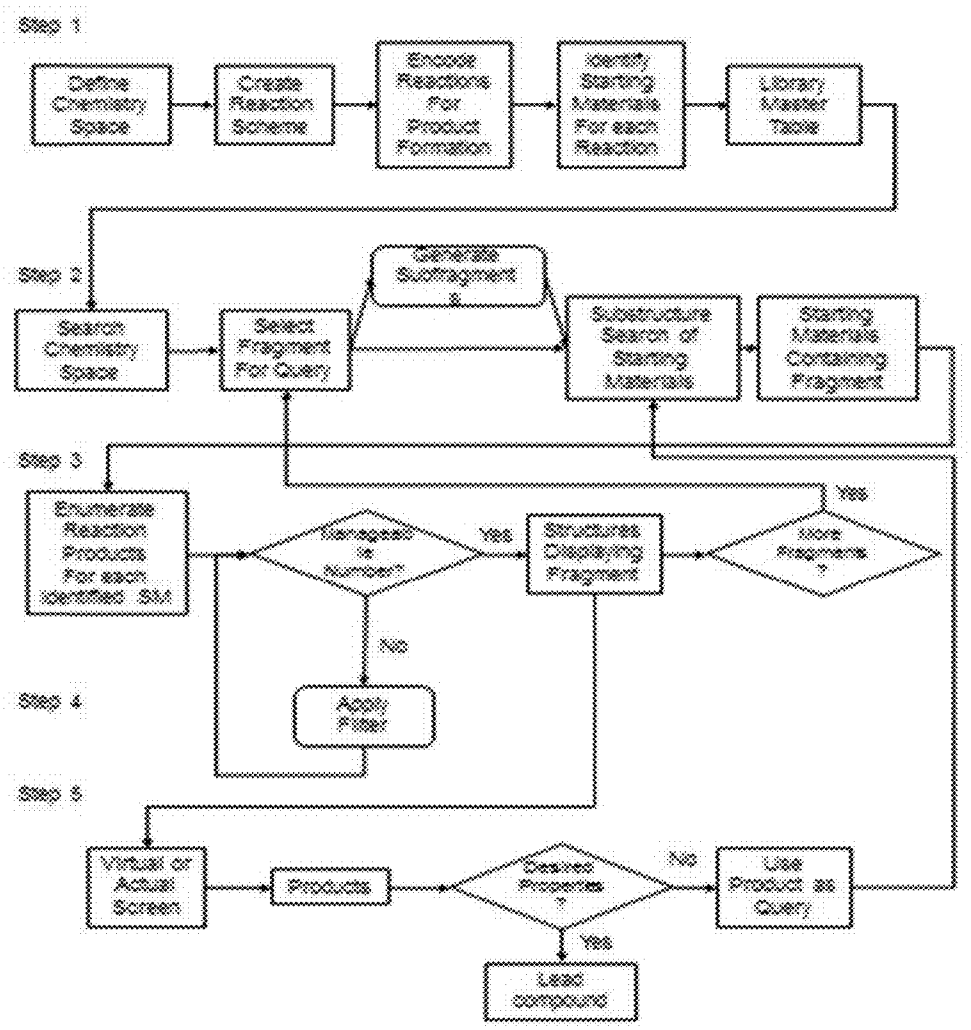
FIG. 1 illustrates an exemplary method, or process, of the invention.

In alternative embodiments, the invention provides methods of making compounds, and libraries of compounds, using a "feasible reaction" growth scheme. In alternative embodiments, the invention provides methods for searching a chemistry space, including a chemistry space comprising the collection of all compounds that can be made by current synthetic methods, for example, the chemistry space from the SYNTHEVERSE™ chemistry space (see e.g., Lemmen, et al. (2011) Abstracts of Papers, 241st ACS National Meeting & Exposition, Anaheim, Calif., United States, Mar. 27-31, 2011) using a fragment of lower (lesser) complexity to identify a manageable set of products (e.g., lead compounds, drugs or drug candidates) that display the fragment in a variety of structural contexts limited only by the size of the implemented chemistry space. In one embodiment, the fragment (for example, in alternative embodiments, is a single ring or a ring assembly), is used to search a starting material by substructure; a subset of starting materials is identified that contain the fragment or the fragment substructure.

In alternative embodiments, these products are then subjected to a virtual screen or are synthesized and assayed by a fragment screening assay or a biological or a chemical or other assay. In one embodiment, the invention provides methods for identifying desirable compounds, e.g., biological compounds or drugs or drug candidates, from compound sets (e.g., very large compound sets, such as a SYNTHEVERSE™ chemistry space) using a compound fragment as the query.

In alternative embodiments, the methods use a chemistry space, or a plurality of synthesizable product molecules, or a plurality of synthetic compounds, wherein the synthesizable product molecules are defined or described as a set of reactions, or a set of "feasible" reactions, with a set of starting materials associated with each reaction, and each reaction step of each reaction sequence is encoded separately so that intermediate structures are available as products in the chemistry space. In alternative embodiments, a "feasible reaction" is defined as one where there exists direct or analogous literature precedent for producing the desired product from the defined starting materials whether or not the reaction has been physically attempted. For example, even though a Suzuki coupling between a particular boronic acid and aromatic bromide has not been described, the reaction would be feasible if both starting materials had been used in other successful Suzuki couplings. Likewise, even though no Suzuki coupling with a particular boronic acid has been reported, the reaction with an aromatic bromide would still be feasible if successful Suzuki couplings had been performed on related boronic acids, for example a regioisomer. In alternative embodiments, reagent sets associated with a particular reaction in a SYNTHEVERSE™ chemistry space are selected so that the possible combinations define feasible reactions. It will be evident to those skilled in the art that there are reactions that, for the purposes of the SYNTHEVERSE chemistry space, may be considered feasible but that are not readily practicable.

In alternative embodiments, the method steps comprise:

1) Providing a chemistry space of synthesizable product molecules, described as a set of reactions with a set of starting materials associated with each reaction. Each reaction step of each reaction sequence is encoded separately so that intermediate structures are available as products in the space. Also encoded separately for each reaction are a set of starting materials that produce products that cannot be used in subsequent steps of the reaction scheme.

Examples of reactions include, but are not limited to, palladium mediated cross-coupling reactions such as the Suzuki, Negishi and Stille reactions, amine acylation, amine sulfonylation, nucleophilic displacement of an aromatic halogen, reduction, oxidation, alkylation of an amine, oxygen or carbon nucleophile, reductive amination, the Mitsonobu reaction, the Cadogan reaction, olefin metathesis, heterocyclic ring condensations, electrophilic aromatic substitution and the like.

Examples of reagent classes that would serve as the set of starting materials for a specific reaction include, but are not limited to, carboxylic acids, carboxylic acid chlorides, primary amines, secondary amines, sulfonyl chlorides, alcohols, aldehydes, ketones, alkyl halides, aryl halides, boronic acids, trialkyl tin reagents, nitriles, isonitriles, imidates and the like as determined by the requirements of the reaction itself 2) Providing a fragment or a substructure of a fragment (for example, in alternative embodiments, a single ring or ring assembly), which is then used to search the starting material set of the space by substructure. A subset of starting materials is identified that contain the fragment or fragment substructure.

In alternative embodiments, the methods comprise providing a set of simpler fragments generated from the original structure, e.g., by stepwise removal of all atoms not contained in a ring or equivalent structure. The set of all possible combinations that contain at least one non-ring atom can be used to search the starting material set of the space by substructure to generate the starting material subset.

3) Product structures are generated from the identified starting materials in step 2 in all reactions where they are used directly. Because this is a one-step reaction scheme, the number of products per reaction is limited by the number of starting materials.

4) The products from step 3 are filtered to a manageable number for a virtual screen or synthesis and assay. Possible filters include, but are not limited to, reactive functional group removal, property limits, clustering and selection, or random percent selection, or a combination thereof 5) In alternative embodiments, the filtered products are then further screened by a virtual screen or actual screening assay for purchased or synthesized compounds to identify products with desirable profiles.

6) Any product identified in step 4 or step 5 can then be used as a query for step 2. In this case, the reactions being searched contain the product as a starting material and the new products identified can be synthesized by a reaction scheme of two steps or more.

7) In alternative embodiments, the process can be applied again to any product of step 6, identifying a small subset of interest related to the initial fragment out of the entire chemistry space.

8) This process can be repeated through step 7 for all fragments of interest, leading to a set of compounds with desirable profiles (e.g., a biological or a chemical property or activity) derived from the original chemistry space. These products retain the design characteristics of the original space and are associated with a reaction scheme for their synthesis and the required starting materials.

In alternative embodiments, the method steps comprise:

1) Providing a fragment or a substructure of a fragment (for example, in alternative embodiments, a single ring or ring assembly) for which a substructure search of the starting material set of the space described in step 1 above returns no hits.

2) Determining the reactions where this fragment or substructure could react and is used directly.

3) Generating the product structures using the structure described in step 1 as the only representative of its reagent list and all the starting materials used for the other lists in each reaction identified in step 2. Because this is a one-step reaction scheme and the fragment is not present in the original space, the number of products per reaction is limited by the number of starting materials of the other reactant types.

4) The products from step 3 are filtered to a manageable number for a virtual screen or synthesis and assay. Possible filters include, but are not limited to, reactive functional group removal, property limits, clustering and selection, or random percent selection, or a combination thereof 5) In alternative embodiments, the filtered products are then further screened by a virtual screen or actual screening assay for purchased or synthesized compounds to identify products with desirable profiles.

6) Any product identified in step 4 or step 5 can then be used as a query for step 1. In this case, the reactions being searched contain the product as a starting material and the new products identified can be synthesized by a reaction scheme of two steps or more. Again, because the original starting material was not in the chemistry space, the generated products were also not present in the original chemistry space.

7) In alternative embodiments, the process can be applied again to any product of step 6, identifying a small subset of interest related to the initial fragment that is an extension of the original chemistry space.

8) This process can be repeated through step 7 for any fragment that contains functionality that can react in the reaction schemes described for the space, leading to a set of compounds with desirable profiles (e.g., a biological or a chemical property or activity). These products extend the design characteristics of the original space but are still associated with a reaction scheme for their synthesis and the required starting materials.

In alternative embodiments, the method steps comprise:

3) Product structures are generated from the identified starting materials in step 2 above in all reactions where they are used in a primary intermediate (an intermediate made only from described starting materials). Because this is a two-step reaction scheme, the number of intermediates per reaction is limited by the number of starting materials in the other reagent lists. In this case, the smallest number of products that contains each of the possible starting materials is generated. For example, if the two-step reaction scheme is:

A+B→Intermediate C

C+D→product E and there are 5 A starting materials, 10 B starting materials and 24 D starting materials, then the total number of products E is 5×10×24=1200. If $A_3$ is the starting material of interest, then there are 240 possible E containing all the combinations of B and D. In this case, intermediate C is enumerated 12 times to give $A_3B_1$, $A_3B_2$ . . . $A_3B_{10}$, $A_3B_1$, $A_3B_2$. C is then combined with each individual D to generate 24 E: $A_3B_1C_1$, $A_3B_2C_2$, . . . $A_3B_{10}C_{10}$, $A_3B_1C_{11}$, . . . $A_3B_{10}C_{20}$, $A_3B_{10}C_{21}$, $A_3B_{10}C_{22}$ 4) The remainder of the steps are performed as above.

In alternative embodiments, the method steps comprise:

1) Providing a fragment or a substructure of a fragment (for example, in alternative embodiments, a single ring or ring assembly) for which a set of related compounds is desired by comparison to a calculated property or properties.

2) Determining the desired range of each property relative to the initial query. For example, low or higher molecular weight, low or higher ring count, lower or higher AlogP.

3) Generating all product structures that match the calculated property ranges. For each library, the properties are corrected for the changes produce by each reaction so that the properties measured are based on the product to be generated. Because this query has no structural component, the number of products depends on the size range of the desired properties. Optionally, the number of products that will be generated can be determined before enumeration and the ranges adjusted until a manageable number can be produced.

4) The products from step 3 are filtered to a manageable number for a virtual screen or synthesis and assay. Possible filters include, but are not limited to, reactive functional group removal, property limits, clustering and selection, or random percent selection, or a combination thereof 5) In alternative embodiments, the filtered products are then further screened by a virtual screen or actual screening assay for purchased or synthesized compounds to identify products with desirable profiles.

6) Any product identified in step 4 or step 5 can then be used as a query for step 2. In this case, the properties ranges being used are for the product of the previous steps.

7) In alternative embodiments, the process can be applied again to any product of step 6, identifying a small subset of interest with properties related to the initial fragment out of the entire chemistry space.

8) This process can be repeated through step 7 for all fragments of interest, leading to a set of compounds with desirable profiles (e.g., a biological or a chemical property or activity) derived from the original chemistry space. These products retain the design characteristics of the original space and are associated with a reaction scheme for their synthesis and the required starting materials.

Computer Systems and Data Storage Devices

In alternative embodiments, methods of the invention comprise computer implemented methods in whole or in part, and/or implementation using a machine, computer systems or equivalent, within which a set of instructions for causing the computer or machine to perform any one or more of the protocols or methodologies of the invention may be executed. In alternative embodiments, the invention provides computer-implemented methods, computer program products or non-transitory computer program products, Graphical User Interface (GUI) computer program products, computer systems, non-transitory memory medium, computer program storage devices, computer-readable storage media and computers or equivalent electronic system.

In alternative embodiments, the invention (e.g., the computer-implemented methods, computer program products or non-transitory computer program products, Graphical User Interface (GUI) computer program products, computer systems, non-transitory memory medium, computer program storage devices, computer-readable storage media and computers or equivalent electronic systems of the invention) may be practiced by connection or inter connection to or with (e.g., networked), or (e.g., non-transitorily) storaged in or stored on: one or several other machines, e.g., in a Local Area Network (LAN), an intranet, an extranet, or the Internet (e.g., the "cloud"), or any equivalents thereof. The machine, LAN, intranet, extranet, Internet or "cloud", or equivalents thereof, may operate in the capacity of, or in place of, a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, a virtual machine residing on any of these devices or on a remote cloud computing platform, or any machine capable of executing a set of instructions (sequential or otherwise) that specify actions to be taken by that machine. The term "machine" shall also be taken to include any collection of machines, computers or products of manufacture that individually or jointly execute a set (or multiple sets) of instructions to perform any one or more of the methodologies of the invention.

In alternative embodiments, a user or groups of users can practice the invention (e.g., making or identifying a plurality or a library of compounds having a desired property, such as a biological activity or chemical property, or a method for making or identifying a drug or a lead compound having a desired property, such as a biological activity or chemical property) by interacting with or by connection or inter connection to or with (e.g., networked), or (e.g., non-transitorily) storaged in or stored on: one or several other machines, e.g., in a Local Area Network (LAN), an intranet, an extranet, or the Internet (e.g., the "cloud"), or any equivalents thereof, which can have products of the invention, e.g., non-transitory computer program products, Graphical User Interface (GUI) computer program products, non-transitory memory medium of the invention, and the like, interactively and/or intransiently stored thereon. Thus, in alternative embodiment the user can remotely make or identify a plurality or a library of compounds having a desired property.

For example, in alternative embodiments different computing clouds which rely on different technologies can be used to practice the invention, e.g., as described in U.S. patent app. pub. nos. 2012317083, 20130238805, or 20130232470; or, by using Application Programming Interfaces (APIs), virtualization platforms (so-called hypervisors) or resource description formats (e.g., for Virtual Machines, VMs), or any environment offered by the clouds (e.g., with respect to networking), for example, from cloud provider to cloud provider. In alternative embodiments a public or private cloud can be used to practice the invention, for example: VMware with their own hypervisor, the vCloud and vSphere APIs and a proprietary format for virtual machines, Amazon with Xen as hypervisor, the EC2 and S3 APIs and their own proprietary AMI format for virtual machines, or Eucalypthus with KVM or Xen as hypervisor, the EC2 and S3 API and the proprietary EMI virtual machine format, and the like. In alternative embodiments, to create cloud computing resources to practice this invention, a customized virtual machine image is first defined locally for the service to the used; this image is then uploaded ("deployed") via the API to the computing cloud. As a next step, a new virtual machine is started (sometimes also referred to as "deployed") in the cloud, again via the API, from that image. Afterwards, some cloud technologies, e.g., VMware, allow for a certain customization of the deployed virtual machine by executing a customization script. Similar deployment approaches can be utilized for other virtual resources (e.g., for cloud storage or networking resources).

In alternative embodiments, cloud computing allows the delivery or user access of the computer-implemented methods, the computer program products or non-transitory computer program products, the Graphical User Interface (GUI) computer program products, the computer systems, the non-transitory memory medium, the computer program storage devices, the computer-readable storage media and the computer or equivalent electronic systems of the invention, as a service rather than a product, so that shared resources, software, and information can be provided as, e.g., a timed or metered service over a network, e.g., the Internet. Computation, software, data access, and storage resources can be provided without requiring users to know details of the computing infrastructure. In alternative embodiments computing infrastructures used to practice this invention could comprise: servers, data storage devices, networking equipment and software for information technology infrastructure management, automation and orchestration. In alternative embodiments, end-users are allowed to access cloud based enterprise applications through a web browser or a mobile app, which can be account or password limited.

For example, in alternative embodiments, a user or a client can access a remote cloud computing platform by means of a communications network. The user or client may be able to upload or modify data by means of an application running on the user or client's system, such as a general purpose web browser or a specialized application. The application can interface with a remote computing platform by means of a communication network, wherein the communication network may be the Internet, an intranet, or a restricted network and the like. In alternative embodiments, a remote cloud computing platform can be a cluster of one or more computational nodes, including a central node, or name node, e.g., where a directory tree of files that are stored in the file system is kept. If the cloud platform comprises one or more resource nodes in addition to a central node, the central node may track or synchronize data across the one or more remote nodes. Multiple copies of the same set of data may be stored across the one or more remote nodes in order to provide redundancy in the event of unexpected data loss in any node.

In alternative embodiments, cloud computing comprises a remote cloud computing platform, e.g., comprising a distributed architecture that consists of a central node and associated data storage racks, and optionally further comprising a set of one or more remote computational resources nodes. These remote nodes may be in operational communication with each other, and with the central node by means of a communication network such as the internet, or an intranet. The remote nodes may store copies of the stored set of data in order to provide a level of data redundancy. The data in these nodes can be synchronized with a central node.

In alternative embodiments, an exemplary computer system of the invention comprises a processing device (processor), a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), and a data storage device, which communicate with each other via a bus.

In alternative embodiments, a processor represents one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. In alternative embodiments the processor is configured to execute the instructions (e.g., processing logic) for performing the operations and steps discussed herein.

In alternative embodiments the computer system further comprises a network interface device. The computer system also may include a video display unit (e.g., a liquid crystal display (LCD) or a cathode ray tube (CRT)), an alphanumeric input device (e.g., a keyboard), a cursor control device (e.g., a mouse), and a signal generation device (e.g., a speaker).

In alternative embodiments, the invention provides databases as a storage medium for the SYNTHEVERSE™ chemistry space. In alternative embodiments, the invention provides databases comprising or having stored thereon (e.g., as a storage medium for) a compound, or a plurality of compounds, or libraries of compounds, made by a method of the invention. These databases can further comprise (e.g., as a storage medium for) a SYNTHEVERSE™ chemistry space, or a database of starting materials and reactions or a chemistry space, or a plurality of synthesizable product molecules, or a plurality of synthetic compounds. In alternative embodiments, the invention provides systems, computers or equivalent electronic systems, computer program storage devices, computer-readable storage medium and the like comprising or having stored therein or thereon (e.g., as a storage medium for) a database of the invention, and/or a compound, or a plurality of compounds, or libraries of compounds, made by a method of the invention, and these can further comprise a SYNTHEVERSE™ chemistry space, and/or a database of starting materials and reactions or a chemistry space, or a plurality of synthesizable product molecules, or a plurality of synthetic compounds.

In alternative embodiments, the data storage device (e.g., drive unit) comprises a computer-readable storage medium on which is stored one or more sets of instructions (e.g., software) embodying any one or more of the protocols, methodologies or functions of this invention. The instructions may also reside, completely or at least partially, within the main memory and/or within the processor during execution thereof by the computer system, the main memory and the processor also constituting machine-accessible storage media. The instructions may further be transmitted or received over a network via the network interface device.

In alternative embodiments the computer-readable storage medium is used to store data structure sets that define user identifying states and user preferences that define user profiles. Data structure sets and user profiles may also be stored in other sections of computer system, such as static memory.

In alternative embodiments, while the computer-readable storage medium in an exemplary embodiment is a single medium, the term "machine-accessible storage medium" can be taken to include a single medium or multiple media (e.g., a centralized or distributed database, and/or associated caches and servers) that store the one or more sets of instructions. In alternative embodiments the term "machine-accessible storage medium" can also be taken to include any medium that is capable of storing, encoding or carrying a set of instructions for execution by the machine and that cause the machine to perform any one or more of the methodologies of the present invention. In alternative embodiments the term "machine-accessible storage medium" shall accordingly be taken to include, but not be limited to, solid-state memories, and optical and magnetic media.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The following examples are provided to further illustrate the invention but not to limit its scope. Other variants of the invention will be readily apparent to one of ordinary skill in the art.

EXAMPLES

Standard procedures and chemical transformation and related methods are well known to one skilled in the art, and such methods and procedures have been described, for example, in standard references such as *Fiesers' Reagents for Organic Synthesis*, John Wiley and Sons, New York, N.Y., 2002*; Organic Reactions*, vols. 1-83, John Wiley and Sons, New York, N.Y., 2006; March J. and Smith M., *Advanced Organic Chemistry,* 6th ed., John Wiley and Sons, New York, N.Y.; and Larock R. C., *Comprehensive Organic Transformations*, Wiley-VCH Publishers, New York, 1999. All texts and references, patents and patent applications cited herein are expressly incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. Examples suitable protecting groups that can be used to practice this invention can be found in e.g., T. W. Greene, *Protecting Groups in Organic Synthesis,* 3rd edition, John Wiley & Sons, Inc. 1999; or T. W. Greene and P. G. M. Wuts, *Protecting Groups in Organic Synthesis,* 4th edition, John Wiley & Sons, Inc. 2007.

The exemplary protocols were written in PIPELINE PILOT™ version 8.5™ (Accelrys, San Diego, Calif.) (a graphical scientific workflow authoring application) using the CHEMISTRY COLLECTION™ (Accelrys) (a comprehensive suite of capabilities for the manipulation and management of chemical information) components and the MOLECULAR TOOLKIT™ (Accelrys) (a software development kit for accessing and modifying molecular data objects in protocols such as atoms, bonds, molecules, reactions and macromolecules) as needed. A representative set of products incorporating each starting material at least once was enumerated to determine that the scope of each reaction in each library was correct. These enumerated structures, scaling linearly with the number of starting materials in the library definition, were also available for query protocols. Library definitions were summarized as individual rows in a Master Table, shown as Table 1, below. Locations and file names were included in the Master Table so that files could be read directly into the query protocols. Commercial availabilities were determined through use of the DISCOVERYGATE™ (Accelrys) web search as implemented in PIPELINE PILOT 8.5™ (Accelrys). Potential starting materials with at least one reliable vendor were reviewed manually for medicinal chemistry value and price. Functional groups on selected starting materials were modified as necessary to the group or groups required by each reaction definition and added to the Master Table.

Example 1—Exemplary Protocols

This example describes an exemplary protocol of the invention.

The following two fragments are known to bind to the anti-apoptotic protein bcl-XL with the following affinities (see e.g., Petros, A. M. (2006) et al *J Med Chem,* 49:656):

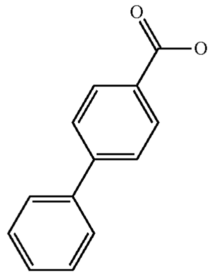

1200 μM

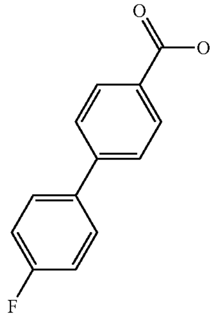

300 μM

Method Step 1

A biased SYNTHEVERSE™ chemistry space was built containing the following 3 step reaction scheme based on the published method for differentiated reactivity between the 2- and 4-bromo of 2,4-dibromobenzoic acid and the known differential selectivity: SNAr substitution of 2-fluoro and 2 chloro benzoic acids with amines vs Buchwald-Hartwig reaction of bromobenzoic acids with amines.

Reaction Scheme Step 1:

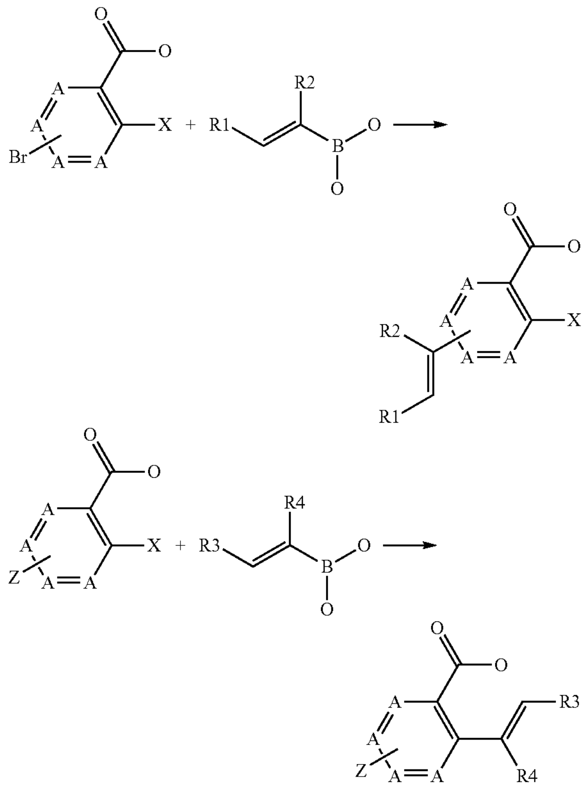

-continued

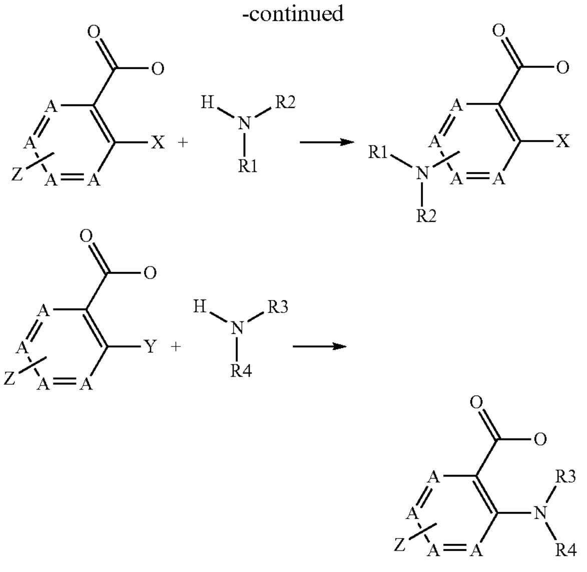

Where A is C or N, X is Cl or Br, Y is F or Cl, and Z is Br or, if attached to a carbon next to an aromatic nitrogen, Cl. The second starting material is a commercially available sp2 hybridized boronic acid or tin reagent including aromatic rings, carbocycles and heterocycles or a primary or secondary aliphatic or aryl amine, protected when necessary with an acid sensitive protecting group such as Boc.

Alternative forms of the boronic acid starting materials, in this case boronic esters and trialkyl tin reagents, were converted to their boronic acid analogs before incorporation into the appropriate reagent list.

Reaction Scheme Step 2:

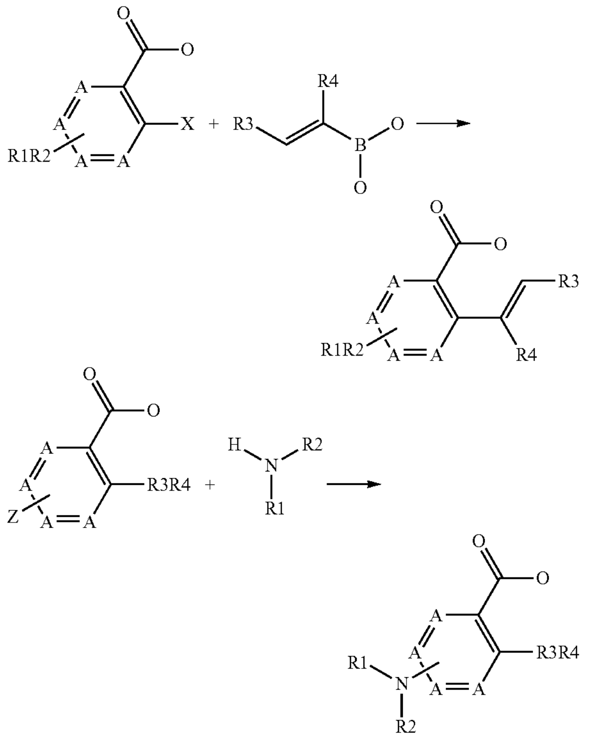

Where R1R2 or R3R4 represents the starting material added in step 1 and the others are have the same definition as for step 1.

Reaction Scheme Step 3:

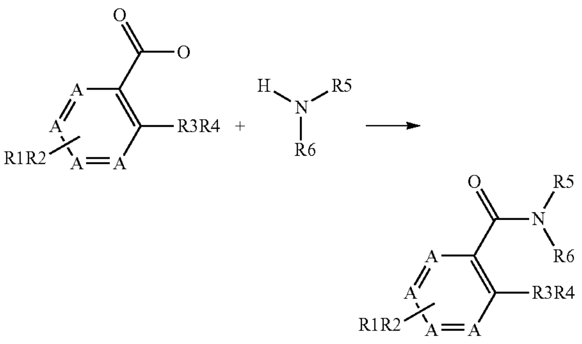

Where the definitions are the same as for step 1 and step 2.

TABLE 1

A master table was generated for the reaction scheme above:

| Library | SM 1 | SM2 | Rxn file | Reaction Type | 1 # | 2 # | Product # |
|---|---|---|---|---|---|---|---|
| BB_30000 | BB_30000_Core | BB_30000_Boronate | BB_30000 | Suzuki | 106 | 201 | 21,306 |
| BB_30001 | BB_30001_Core | BB_30001_Boronate | BB_30001 | 2BrCOOH Suzuki | 12 | 201 | 2,412 |
| BB_30002 | BB_30002_Core | BB_30002_Amine | BB_30002 | Buchwald-Hartwig | 115 | 334 | 38,410 |
| BB_30003 | BB_30003_Core | BB_30003_Amine | BB_30003 | SNAr | 9 | 1200 | 10,800 |
| BB_30004 | BB_30004_Core | BB_30004_Amine | BB_30004 | SNAr | 44 | 1200 | 52,800 |
| BB_30005 | [BB_30001] | BB_30005_Boronate | BB_30005 | Suzuki | 2412 | 201 | 484,812 |
| BB_30006 | [BB_30001] | BB_30006_Amine | BB_30006 | Buchwald-Hartwig | 2412 | 334 | 805,608 |
| BB_30007 | [BB_30003] | BB_30007_Boronate | BB_30007 | Suzuki | 1200 | 334 | 400,800 |
| BB_30008 | [BB_30003] | BB_30008_Amine | BB_30008 | Buchwald-Hartwig | 10800 | 334 | 3,607,200 |
| BB_30009 | [BB_30005] | BB_30004_Amine | BB_30009 | Amide Coupling | 484812 | 1200 | 581,774,400 |
| BB_30010 | [BB_30006] | BB_30004_Amine | BB_30010 | Amide Coupling | 805608 | 1200 | 966,729,600 |
| BB_30011 | [BB_30007] | BB_30004_Amine | BB_30011 | Amide Coupling | 400800 | 1200 | 480,960,000 |
| BB_30012 | [BB_30008] | BB_30004_Amine | BB_30012 | Amide Coupling | 3607200 | 1200 | 4,328,640,000 |

In the table, the columns SM 1 and SM 2 contain the names of the files of commercially available starting materials selected for being medicinally interesting and for their ability to perform the specified reaction. SM1 in square brackets represents using the products of the previous library. The numbers of SM are shown in the # columns, and the total number of combinatorial products is shown in the last column. By design, BB_30000 contains products that can be produced by a single Suzuki reaction but cannot serve as a starting material for Step 2, while BB_30001 represents a smaller set that can be elaborated in step 2. There are approximately 126,000 products of Step 1, 5.3 million products of Step 2 and over 6 billion products of Step 3.

Method Step 2

The initial fragment contained more than one ring, so a substructure search was performed on the reagents included in the chemistry space using fluorobenzene:

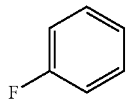

as the query.

From the set of 1572 unique starting materials in the chemistry space, 106 reagents contained the fluorobenzene substructure. Four libraries contained these starting materials BB_30000, BB_30002, BB_30003, and BB_30004. Representative examples of the starting materials are shown in the figure below.

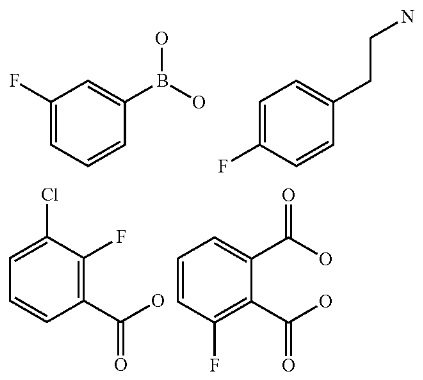

-continued

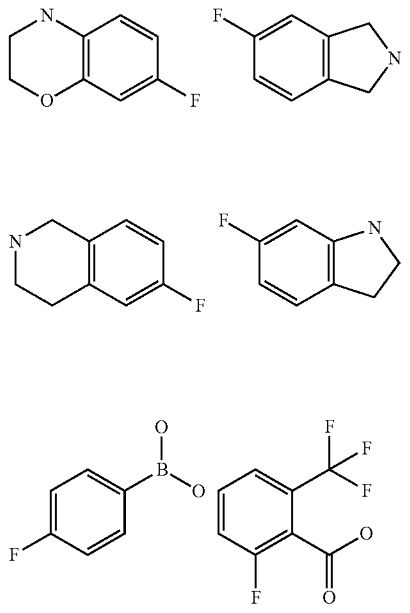

-continued

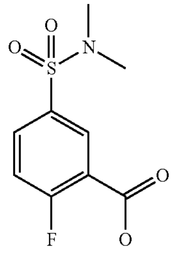

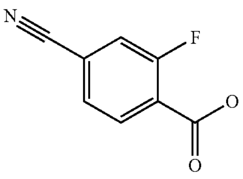

Method Step 3

Using the reactions from the master table, 24,729 products that contain the fluorophenyl group somewhere in their structure were generated from the four libraries.

Representative products are shown in the figure below:

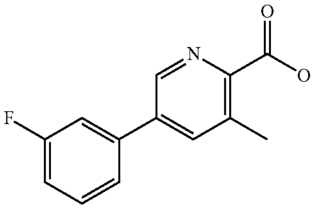

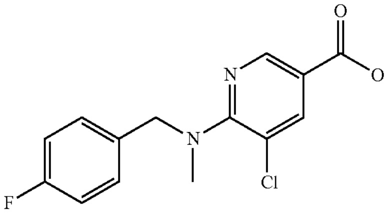

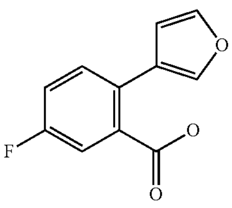

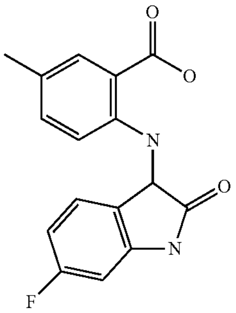

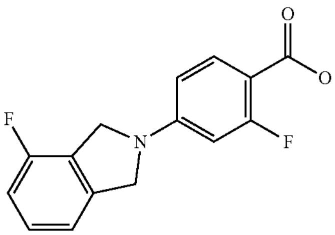

-continued

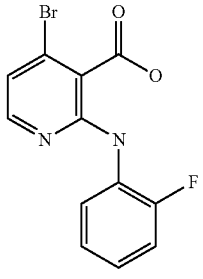

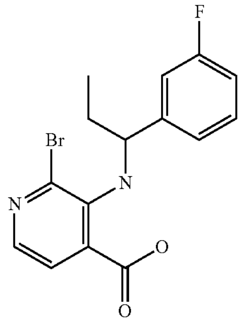

Chiral

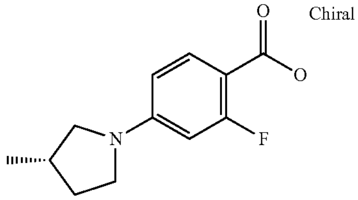

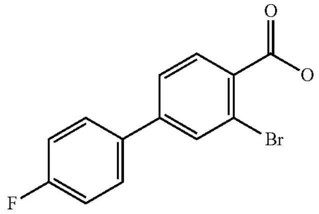

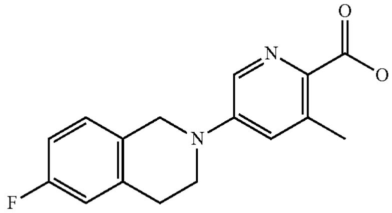

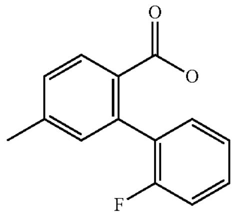

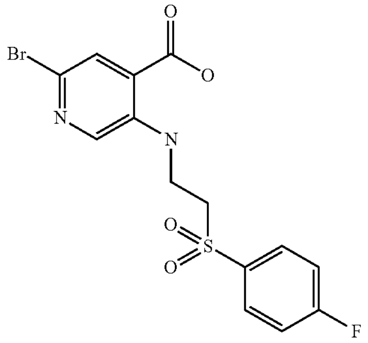 [SMILES: O=C(O)c1cc(Br)ncc1NCCS(=O)(=O)c1ccc(F)cc1]

Method Step 4

The products are filtered to remove compounds containing the 2-fluoroacid functional group (10,978 removed) to generate the list of products. The representative products with the undesired compounds removed are shown in the figure below.

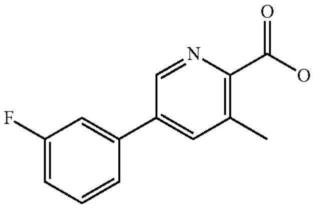

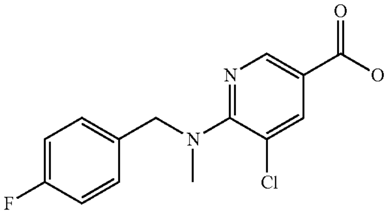

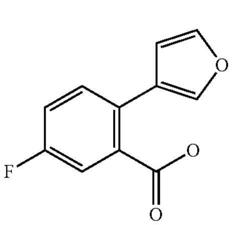

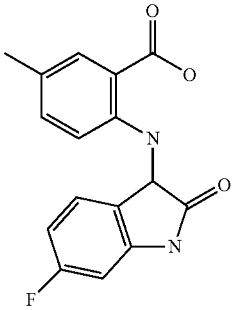

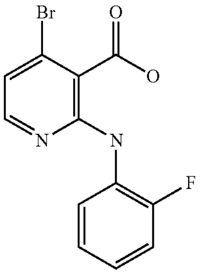

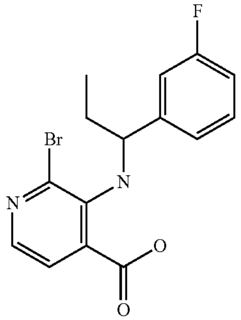

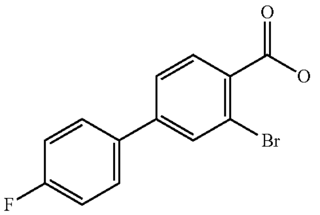

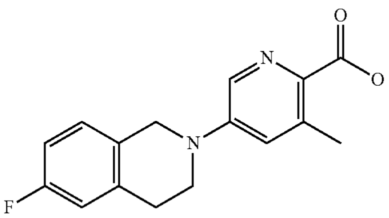

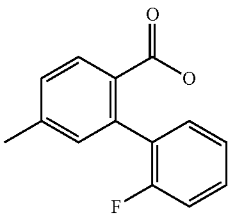

-continued

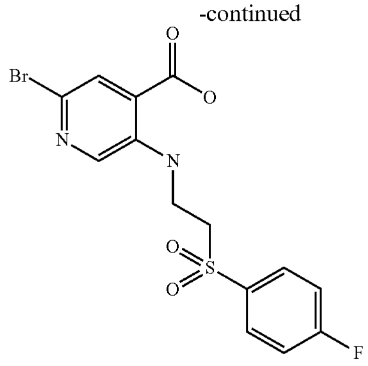

Method Step 5

The remaining 13,751 compounds are submitted to a virtual screen. In a first screen, the compounds were filtered to contain the functional groups of the original literature structure in the same relative positions. 32 compounds from libraries BB_30000 and BB_30001 pass this filter. Representative compounds similar to active molecules reported in the literature are shown in the figure below.

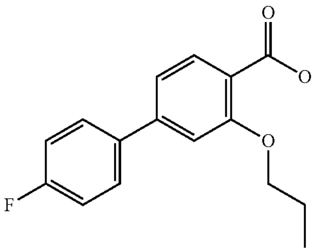

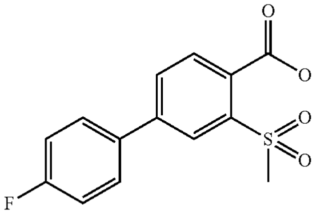

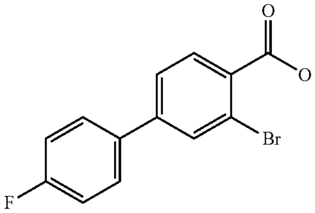

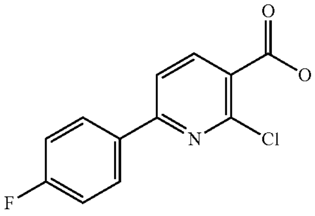

In a second screen, the compounds were filtered to contain the 4-fluorophenyl boronic acid starting material required to make the original literature structure by the reaction schemes in this library. 249 compounds from libraries BB_30000 and BB_30001 pass this filter.

Figure 2:
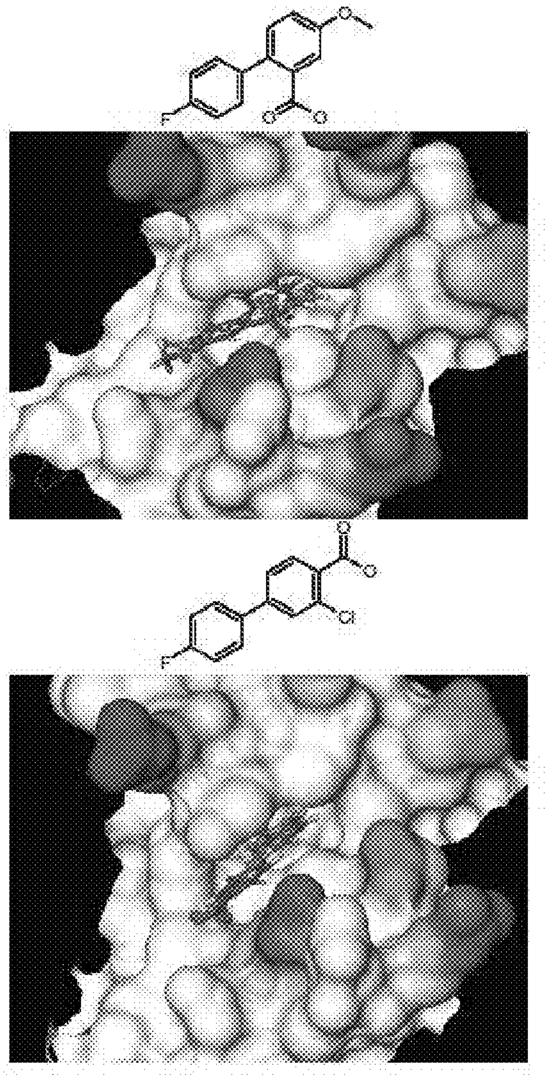
FIG. 2 illustrates representative virtual structure compounds as identified by the exemplary process (method) of the invention as described in Example 1, below, with the docked conformation compared to the bound literature compound below each structure.
Figure 3:
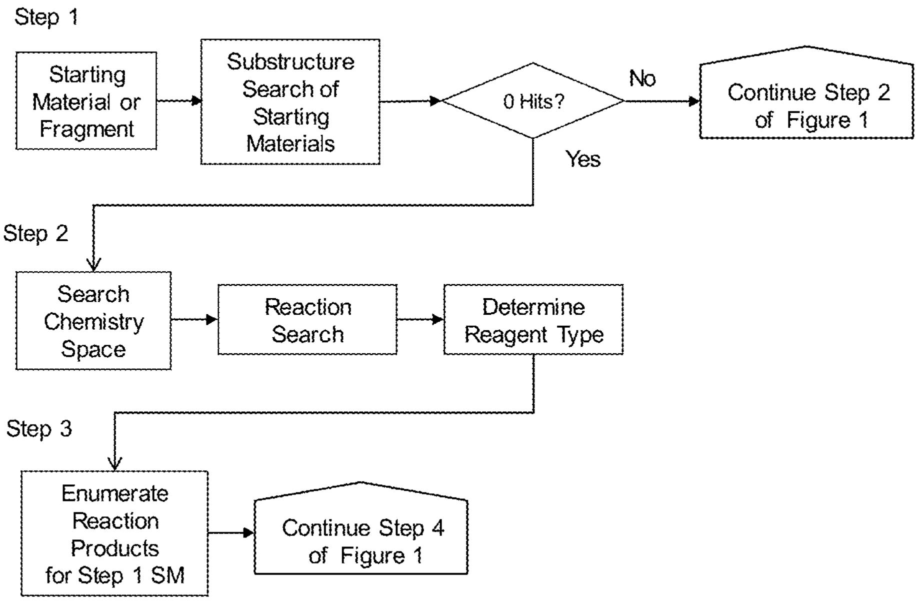
FIG. 3 illustrates an exemplary method, or process, of the invention, which can be used alone or in conjunction with the exemplary method of FIG. 1, or any method of this invention.

The 249 compounds were submitted to a virtual screen comprised of computing a 3-D FEATURETREES™ similarity score to the bound conformation of the literature molecule (Protein Data Bank accession code 1YSG) using FLEXS™ (BioSolveIT, GmbH, Sankt Augustin, Germany), followed by docking of the compounds with similarities >90% at the binding site of the literature compound in the 1YSG complex using LEADIT™ (BioSolveIT). The resulting virtual structures were compared visually to the experimentally-derived conformation of the bound literature hit. 99 structures passed the 3D similarity filter and 8 were chosen as potential candidates for synthesis and binding affinity measurement. Representative virtual structure compounds are shown in FIG. 2 with the docked conformation compared to the bound literature compound below each structure.

Example 2—Alternative Filters—Exemplary Protocols

This example describes an alternative exemplary protocol of the invention.

Method Step 4

The products from example 1 step 3 with the 2-fluoroacid functional group removed (13,751 compounds) were filtered further by assessing their commercial availability. In the ACD (Available Chemicals Directory from Accelrys (San Diego, Calif.), accessed through DISCOVERYGATE™ 3/2013), 552 compounds were listed with a numerical price. This set was filtered further by passing only compounds containing 14 to 17 heavy atoms (−2 to +1 from the query). This filter set does not conserve number of rings or aromaticity in the product set. Representative compounds from the 266 compounds passing the last filter are shown in the figure below.

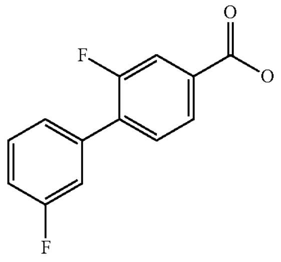

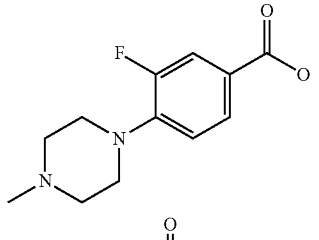

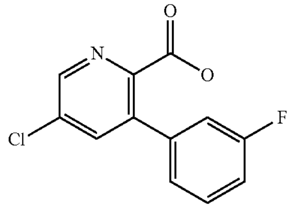

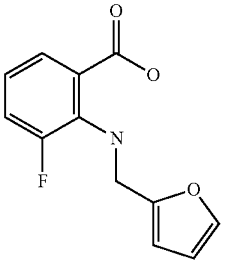

-continued

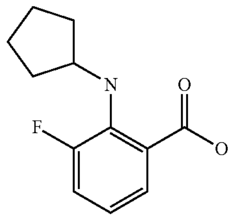

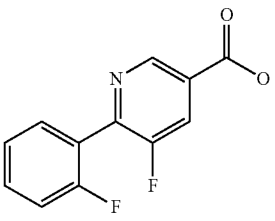

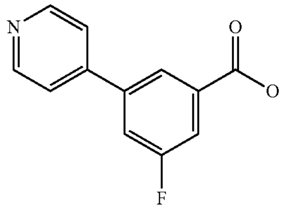

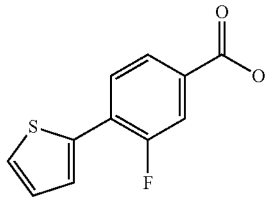

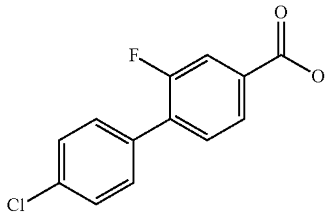

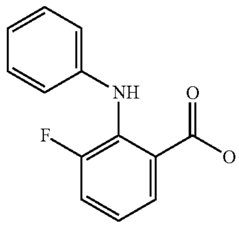

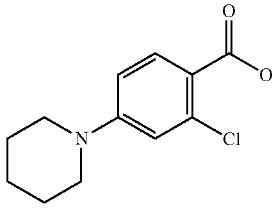

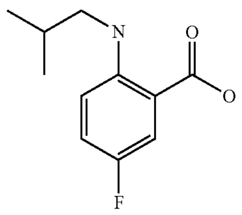

From this set, a set of 11 compounds was selected for purchase based on vendor, diversity of rings, and the presence of 1 fluorine atom on the molecule. The three compounds from the representative set above that were chosen are shown below.

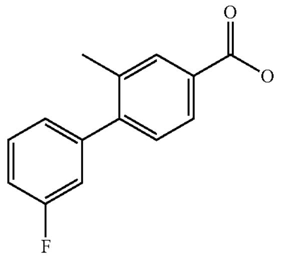

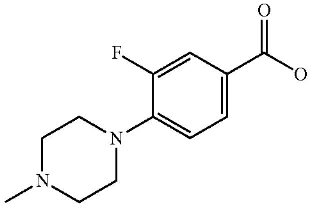

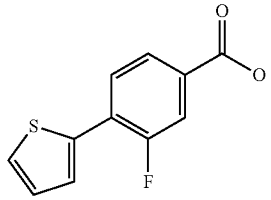

Example 3—Additional Starting Material—Exemplary Protocols

This example describes an alternative exemplary protocol of the invention.

Method Step 2

The biased SYNTHEVERSE™ chemistry space from Example 1 was queried with (S)-(+)-3-fluoropyrrolidine, representing an alternative fragment substructure. In this space, there are no hits from a substructure search with this query. However, (S)-(+)-3-fluoropyrrolidine belongs to the general class of secondary amines that were used as a reagent in multiple reactions in the master table. The SYNTHEVERSE™ chemistry space products generated from (S)-(+)-3-fluoropyrrolidine in one reaction step were generated by the following procedure:

a. (S)-(+)-3-fluoropyrrolidine was evaluated for permissible reaction in each line of the Master Table that contained first step products.

b. For each reaction where (S)-(+)-3-fluoropyrrolidine could react, the reagent column for the new reagent was determined by combinatorial enumeration of a single reagent from each column and (S)-(+)-3-fluoropyrrolidine. The additional product generated contains (S)-(+)-3-fluoropyrrolidine in the correct reagent column.

c. For each reaction from b, all products containing (S)-(+)-3-fluoropyrrolidine were enumerated using it as the only reagent for its reagent column and all possible reagents at the other positions.

In the Example 1 space, there are three libraries which use secondary amines in the first step, BB_30002, BB_30002, and BB_30004. 174 Product were generated from the three sets, of which 117 pass the heavy atom range filter described in example 2. Representative compounds are shown in the figure below.

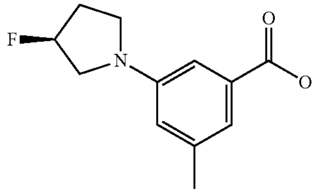

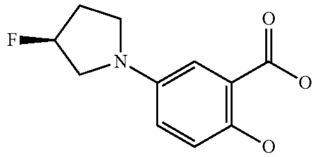

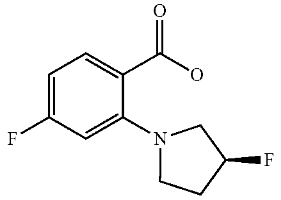

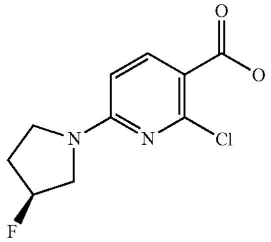

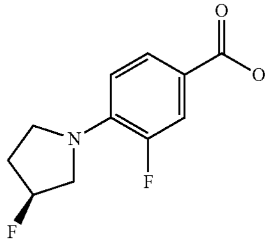

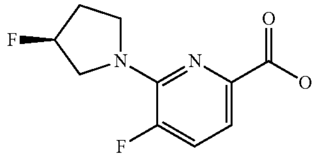

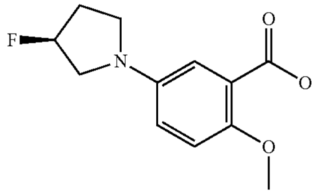

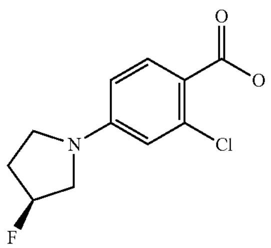

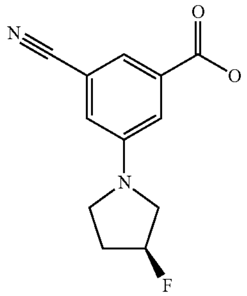

-continued

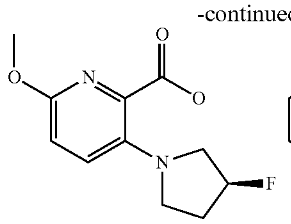

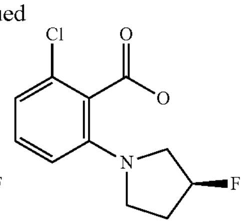

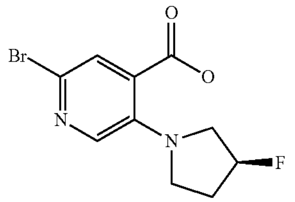

Application of the virtual screening protocol from example 1 would generate a small set (<5) of compounds where (S)-(+)-3-fluoropyrrolidine has replaced another ring previously existing in the original hit set. These compounds can be synthesized and the affinity measured in a binding assay.

Example 4—Query by Property Filters—Exemplary Protocols

This example describes alternative exemplary protocols of the invention.

Method Step 1

A biased SYNTHEVERSE™ chemistry space was built containing the following 2 step reaction scheme based on a published cyclization scheme of beta amino acids:

Reaction Scheme Step 1:

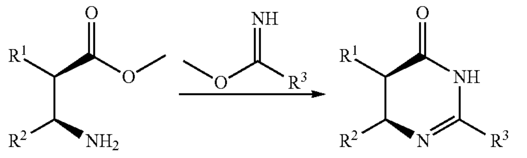

Because the actual availability of the $R^3$ imidates is low, the choice of starting materials was expanded by using the precursor nitriles. 241 compounds were selected and stored internally in the imidate form. A link to the original structure was maintained. Similarly, beta amino acids were available either as the free amino acid, or as various amino esters or as various amino ester salts. 125 acids and esters were selected and stored internally in the free amine methyl ester form. Mono-Boc protected diamino acids were expanded by one additional step in the reagent set to add the dimethylamino, acetamido and methanesulfonamido derivatives. A link to the Boc structure was maintained. The reaction sequence to these derivatives contains one additional step immediately recognized by one of ordinary skill in the art.

Reaction Scheme Step 2:

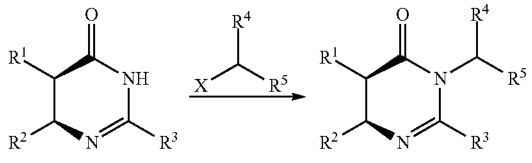

The products of step 1 can be further modified by reaction with a set of 347 moderate to high activity alkylating agents where X is Cl, Br or I.

The library size is 30125 first step products and >10 million second step products. Representative products are shown in the figure below.

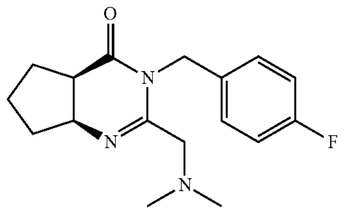

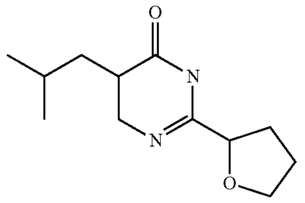

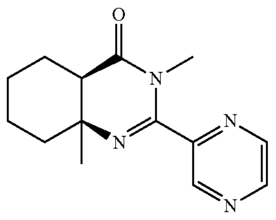

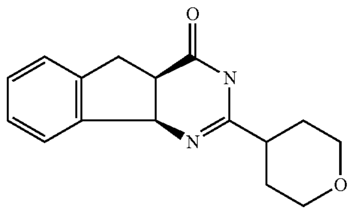

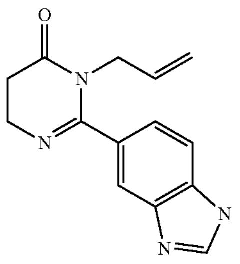

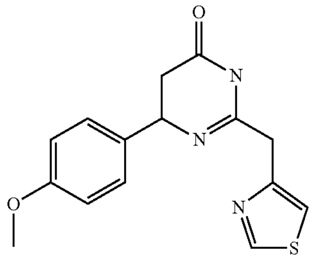

-continued

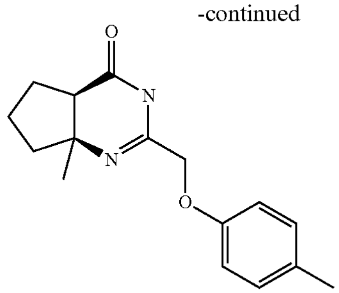

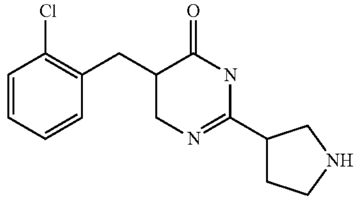

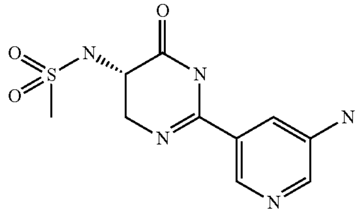

Method Step 2

An initial fragment hit was identified in a hypothetical fragment screen. Generation and testing of a set of fragment analogs in the same fragment screen led to a minimum requirement for activity:

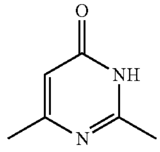

Fragment Hit

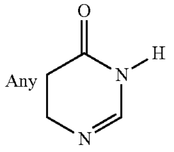

Required for Activity

The biased SYNTHEVERSE™ chemistry space from step 1 was searched by a property query looking for all compounds with no more than 6 additional heavy atoms and at least 1 additional ring compared with the original fragment hit. The ranges used for the query are Num_Atoms+0-+6, Num_Rings>+0.

Method Step 3

The subset containing this range of properties was generated from the SYNTHEVERSE™ library definition. The requirement for an additional ring means that the actual range of atoms for the products generated is +2-+6. 1708 Compounds were produced from this library. Representative structures are shown in the figure below.

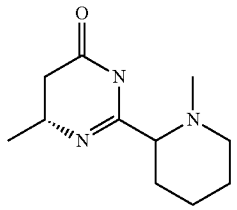

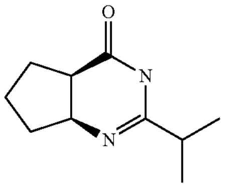

-continued

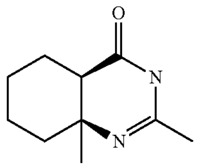

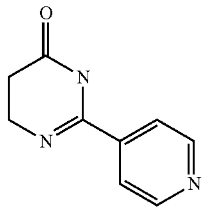

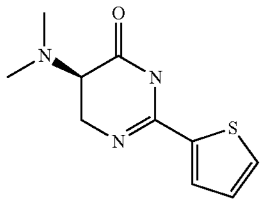

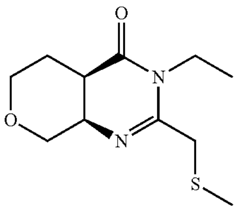

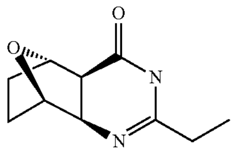

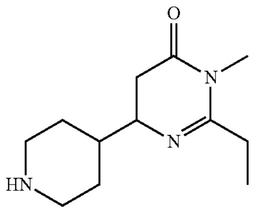

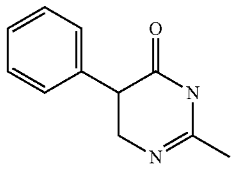

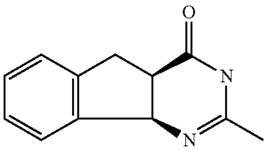

Method Step 4

The products are filtered to remove compounds that did not contain the required features for activity. 870 Products passed this filter. Representative compounds related to the compounds shown in step 3 are shown in the figure below.

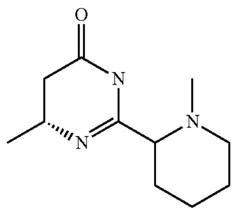

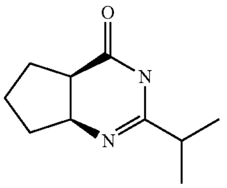

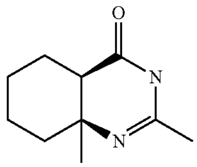

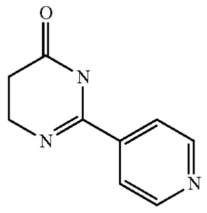

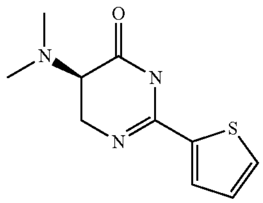

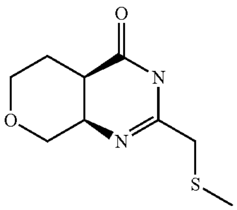

-continued

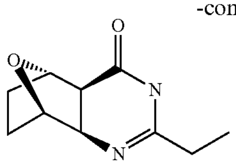

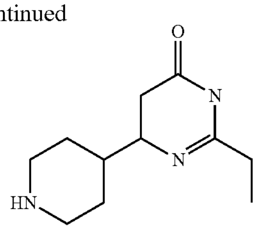

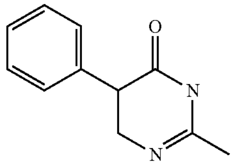

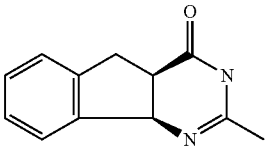

In alternative embodiments, the remaining steps of the method can be performed as described in examples 1 and 2.

Although the foregoing invention has been described in some detail by way of illustration and example for purposes of clarity of understanding, it will be readily apparent to one of ordinary skill in the art in light of the teachings of this application that certain changes and modifications may be made thereto without departing from the spirit or scope of the appended claims. A number of aspects of the invention have been described. Nevertheless, it will be understood that various modifications may be made without departing from the spirit and scope of the invention. Accordingly, other aspects are within the scope of the following claims.

What is claimed is:

1. A method for identifying a plurality or a library of compounds having a selected property, or a method for making or identifying a drug or a lead compound having a selected property, comprising:

(1)

(a) providing a chemistry space, or a plurality of synthesizable product molecules, or a plurality of synthetic compounds, wherein the synthesizable product molecules are defined or described as a set of reactions, with a set of reagent sets or starting materials associated with each reaction, and each reaction step of each reaction sequence is encoded separately so that intermediate structures are available as products in the chemistry space;

(b) providing a fragment or a substructure of a fragment, and searching the starting material set of the chemistry space or a plurality of synthesizable product molecules of step (a) using the fragment or substructure;

(c) generating product compound structures from the identified starting materials in step (b) in all reactions where they are used directly in a one-step reaction scheme, wherein optionally, because this is a one-step reaction scheme, the number of products per reaction is limited by the number of starting materials;

(d) filtering the product compound structures from step (c) to a lesser number, or selecting a subset of the product compound structures from step (c) from a virtual screen, or a combination thereof, and optionally filters comprise reactive functional group removal, property limits, clustering and selection, random percent selection, or a combination thereof;

(e) synthesizing the full set or a subset of the filtered or selected product structures from step (d), and (f) screening the synthetic structures from step (e) by a physical screening assay to identify a plurality of compounds, or a drug, having a selected property or a selected biological activity or chemical property.

2. The method of claim 1, wherein any compound identified in step 1(d) or step 1(f) is used in a query of step 1(b), wherein the reactions being searched contain the product compound structures as a starting material and new product compound structures identified can be synthesized by a reaction scheme of two steps or more.

3. The method of claim 2, wherein the process is applied again to any product of claim 2, and identifying a small subset of interest related to the initial fragment out of the entire chemistry space.

4. The method of claim 3, wherein the process is repeated through claim 3, for all fragments and/or compounds of interest, or having a selected property or biological activity or chemical property, to provide or generate a set of compounds with the selected profile or the selected property derived from the original chemistry space, wherein optionally these products retain the design characteristics of the original chemistry space and are associated with a reaction scheme for their synthesis and the required starting materials, wherein optionally the selected profile or the selected property comprises a selected biological property or activity or chemical property.

5. A method for making or identifying a plurality or a library of compounds having a selected property, or a method for making or identifying a drug or a lead compound having a selected property, comprising:

(1)

(a) providing a fragment or a substructure of a fragment for which a substructure search of the starting material set of the space described in claim 1, step (I)(a), above returns no hits;

(b) determining the reactions where this fragment or substructure could react and is used directly;

(c) generating the product structures using the structure described in step (a) as the only representative of its reagent list and all the starting materials used for the other lists in each reaction identified in step (b), and optionally, where this is a one-step reaction scheme and the fragment is not present in the original space, the number of products per reaction is limited by the number of starting materials of the other reactant types; and (d) the products from step (c) are filtered to a reduced number or selecting a subset of the product compound structures from step (c) from a virtual screen or a combination thereof, and optionally filters comprise reactive functional group removal, property limits, clustering and selection, random percent selection, or a combination thereof;

(2) the method of (1), further comprising: wherein the filtered products are then further screened by synthesis and a physical screening assay to identify products with selected profiles;

(3) the method of (1) or (2), wherein any product identified can then be used as a query for step (I)(a), and optionally, the reactions being searched contain the product as a starting material and the new products identified can be synthesized by a reaction scheme of two steps or more, and optionally, where the original starting material was not in the chemistry space, the generated products were also not present in the original chemistry space;

(4) the method of any of (1) to (3), wherein the process can be applied again to any product of step (3), identifying a small subset of interest related to the initial fragment that are an extension of the original chemistry space;

(5) the method of any of (1) to (4), further comprising: the process can be repeated for any fragment that contains functionality that can react in the reaction schemes described for the space, leading to a set of compounds with selected profiles, and optionally the generated products extend the design characteristics of the original space but are still associated with a reaction scheme for their synthesis and the required starting materials, wherein optionally the selected profile comprises a selected biological property or activity or chemical property;

(6) the method of any of (1) to (5), further comprising: product structures are generated from the identified starting materials in all reactions where they are used in a primary intermediate or an intermediate made only from described starting materials, and optionally, where this is a two-step reaction scheme, the number of intermediates per reaction is limited by the number of starting materials in the other reagent lists, and optionally, the smallest number of products that contains each of the possible starting materials is generated, and optionally, if the two-step reaction scheme is:

A+B→Intermediate C

C+D→product E and there are 5 A starting materials, 10 B starting materials and 24 D starting materials, then the total number of products E is 5×10×24=1200, and optionally, if $A_3$ is the starting material of interest, then there are 240 possible E containing all the combinations of B and D, and optionally if intermediate C is enumerated 24 times to give $A_3B_1$, $A_3B_2$ . . . $A_3B_{10}$, $A_3B_1$, . . . $A_3B_{10}$, $A_3$ $B_1$, . . . $A_3B_4$, C is then combined with each individual D to generate 24 E: $A_3B_1D_1$, $A_3B_2D_2$, . . . $A_3B_{10}D_{10}$, $A_3B_1D_{11}$, . . . $A_3B_{10}D_{20}$, $A_3B_1D_{21}$, . . . $A_3B_4D_{24}$.

6. A method for identifying a plurality or a library of compounds having a selected property, or a method for identifying a drug or a lead compound having a selected property, wherein optionally the selected property comprises a biological activity or chemical property, comprising:

(a) providing a fragment or a substructure of a fragment for which a set of related compounds is determined by comparison to a calculated property or properties, and optionally, the fragment or a substructure comprises a single ring or ring assembly;

(b) determining a desired range of each property relative to the value calculated for the initial query, and optionally each calculated property consists of a molecular weight, a ring count, a AlogP or another property that can be calculated on a per fragment or per atom basis, and optionally the selected range of each property comprises a lower or higher molecular weight, a lower or higher ring count, a lower or higher AlogP, or equivalents, and optionally the selected range of each calculated property may not contain the value calculated for the initial query;

(c) generating all product structures that match the calculated property ranges;

wherein optionally:

(i) for each library, the properties are corrected for the changes produced by each reaction so that the properties measured are based on the product to be generated and because this query has no structural component, the number of products depends on the size range of the selected properties, (ii) the number of products that will be generated can be determined before enumeration and the ranges adjusted until a selected number can be produced;

(iii) the product structures from step (i) or step (ii) are filtered to a reduced number or selecting a subset of the product compound structures from step (i) or step (ii) from a virtual screen, or a combination thereof, and optionally the filters comprise: a reactive functional group removal, property limits, clustering and selection, or random percent selection, or a combination thereof; and (iv) further screening the filtered product structures by synthesis and a physical screening assay for purchased or synthesized compounds to identify products with selected profiles;

(v) the product structure identified in step (iii) or step (iv) is used as a query for step (b), and optionally, the properties ranges used are for the product of the previous steps, and optionally the process can be applied again to any product so identified, (vi) identifying a small subset of interest with properties related to the initial fragment out of the entire chemistry space;

(vii) repeating step (b) and any one of, or subset of, or all of steps (i) to (vi), for all fragments of interest, leading to a set of compounds with selected profiles, optionally a biological or a chemical property or activity, derived from the original chemistry space, wherein the products retain the design characteristics of the original space and are associated with a reaction scheme for their synthesis and the required starting materials.

7. A computer-assisted method comprising a method of claim 1, wherein at least steps a)-d) are implemented by a computer.

8. The method of claim 1, wherein:

(A) the method of step (a) further comprises:

(i) encoded separately for each reaction, a set of starting materials that produce product compound structures that cannot be used in subsequent steps of the reaction scheme, (ii) selecting reagent sets or starting materials associated with a particular reaction in a chemistry space, or a synthetic chemistry space stored on one or more databases, so that all or substantially all possible combinations define feasible reactions;

(iii) wherein the starting materials comprise carboxylic acids, carboxylic acid chlorides, primary amines, secondary amines, sulfonyl chlorides, alcohols, aldehydes, ketones, alkyl halides, aryl halides, boronic acids, trialkyl tin reagents, nitriles, isonitriles, imidates and the like as determined by the requirements of the reaction itself; or, (iv) wherein the reactions comprise: palladium mediated cross-coupling reactions such as the Suzuki, Negishi and Stille reactions, amine acylation, amine sulfonylation, nucleophilic displacement of an aromatic halogen, reduction, oxidation, alkylation of an amine, oxygen or carbon nucleophile, reductive amination, the Mitsonobu reaction, the Cadogan reaction, olefin metathesis, heterocyclic ring condensations, electrophilic aromatic substitution and the like;

(B) the method of step (a) of claim 1 further comprises: steps (i) and (ii); steps (i) and (iii); steps (i) and (iv); steps (ii) and (iii); steps (ii) and (iv); steps (iii) and (iv); steps (i), (ii) and (iii); steps (ii), (iii) and (iv); steps (i), (iii) and (iv); or steps (i), (ii), (iii) and (iv).

9. The method of claim 1, wherein the selected property comprises a biological activity or a chemical property.

10. The method of claim 1, wherein in step (d) a filter comprises: a reactive functional group removal, property limits, clustering and selection, random percent selection, or a combination thereof.

11. The method of claim 5, wherein the selected property comprises a biological activity or a chemical property.

12. The method of claim 5, wherein in step (1)(a) the fragment or a substructure of a fragment comprises a single ring or ring assembly.

13. The method of claim 1, wherein step (b) comprises identifying a subset of starting materials that contain the fragment or the substructure of the fragment.

14. The method of claim 1, wherein the fragment or the substructure of the fragment comprise a single ring or ring assembly or equivalent.

15. The method of claim 1, comprising providing a set of fragments of less complex structure generated from an original or a starting structure, optionally by stepwise removal of some or all atoms not contained in a ring or an equivalent structure.

16. The method of claim 1, wherein the fragment, optionally a single ring or a ring assembly, is used to search the starting material by substructure, and a subset of starting materials is identified that contain the fragment or the fragment substructure, and optionally a fragment comprises or consists of a single ring system that binds with only mM affinity to its target, and optionally the fragment has an ligand efficiency >0.5 kcal/mol/heavy atom, and optionally the set of all possible combinations that contain at least one non-ring atom can be used to search the starting material set of the space by substructure to generate the starting material subset.

* * * * *